US007953624B2

(12) United States Patent
Kunnes

(10) Patent No.: US 7,953,624 B2
(45) Date of Patent: May 31, 2011

(54) SYSTEMS AND METHODS FOR FACILITATING DELIVERY OF CONSULTING SERVICES

(75) Inventor: Richard Kunnes, Dublin, OH (US)

(73) Assignee: P & M Holding Group, LLP, Southfield, MI (US)

( * ) Notice: Subject to any disclaimer, the term of this patent is extended or adjusted under 35 U.S.C. 154(b) by 1243 days.

(21) Appl. No.: 11/333,365

(22) Filed: Jan. 18, 2006

(65) Prior Publication Data

US 2007/0168219 A1     Jul. 19, 2007

(51) Int. Cl.
G06Q 50/00          (2006.01)
(52) U.S. Cl. ............................. 705/7.32; 705/2; 705/7.36
(58) Field of Classification Search ................... 705/2, 7, 705/10
See application file for complete search history.

(56) References Cited

U.S. PATENT DOCUMENTS

| 5,652,842 | A  | * | 7/1997 | Siegrist et al. ..................... 705/2 |
| 6,509,914 | B1 | * | 1/2003 | Babula et al. ................. 715/762 |
| 7,162,427 | B1 | * | 1/2007 | Myrick et al. ................. 705/348 |
| 7,437,303 | B2 | * | 10/2008 | Werblin ............................. 705/2 |
| 7,552,063 | B1 | * | 6/2009 | McEachern ....................... 705/3 |
| 2002/0059088 | A1 |  | 5/2002 | Whalen et al. |
| 2002/0062224 | A1 | * | 5/2002 | Thorsen et al. .................... 705/2 |
| 2002/0072957 | A1 | * | 6/2002 | Thompson et al. ............. 705/10 |
| 2002/0123905 | A1 | * | 9/2002 | Goodroe et al. .................. 705/2 |
| 2002/0173998 | A1 |  | 11/2002 | Case |
| 2002/0174360 | A1 | * | 11/2002 | Ikeda ........................... 713/200 |
| 2004/0054567 | A1 | * | 3/2004 | Bubner ............................. 705/7 |
| 2004/0117214 | A1 | * | 6/2004 | Shea ................................. 705/2 |
| 2005/0021385 | A1 |  | 1/2005 | Lin |
| 2005/0234740 | A1 |  | 10/2005 | Krishnan et al. |
| 2005/0283400 | A1 |  | 12/2005 | Nelson et al. |
| 2006/0235733 | A1 | * | 10/2006 | Marks ............................... 705/7 |
| 2007/0021967 | A1 | * | 1/2007 | Jaligama et al. .................. 705/1 |
| 2007/0038501 | A1 | * | 2/2007 | Lee et al. ........................ 705/10 |
| 2007/0094110 | A1 | * | 4/2007 | McCrea ......................... 705/32 |
| 2007/0129968 | A1 | * | 6/2007 | Johnson et al. .................... 705/2 |
| 2008/0059383 | A1 | * | 3/2008 | Mayernik et al. ............. 705/400 |

OTHER PUBLICATIONS

CMS Forms, The Centers for Medicare & Medicaid Services (CMS), www.cms.hhs.gov, last modified Apr. 1, 2005, retrieved from web.archive.org.*
Carter, Understanding The Time Value of Money, investopedia.com, retrieved Jun. 3, 2010, p. 1-3, http://www.investopedia.com/articles/03/082703.asp.*
The value of healthcare IT, Healthcare Financial Management, vol. 57, No. 1, Jan. 2003 (online reprint p. 1-22).* DeJohn, Group Hunts for weak links in members' supply chains, Hospital Materials Management, vol. 24, No. 6, Jun. 1999, (online reprint p. 1-2).*
International Searching Authority; PCT/US07/00551; International Search Report dated Dec. 20, 2007.
International Searching Authority; PCT/US07/00551; Written Opinion of the International Searching Authority dated Dec. 20, 2007.

* cited by examiner

Primary Examiner — Justin M Pats
(74) Attorney, Agent, or Firm — Dykema Gossett PLLC

(57) ABSTRACT

A method for providing consulting services includes assembling a plurality of solutions or recommendations designed to promote cost savings and improved operational efficiency of a business enterprise, categorizing at least a subset of the plurality of solutions or recommendations into groups, selecting client-relevant solutions, recommendations or groups from the plurality of solutions, recommendations or groups based on information received from the client, prioritizing the client-relevant solutions, recommendations or groups into a prioritized list of client-relevant solutions, recommendations or groups, and successively presenting to the client, over a predetermined amount of time, each of the client-relevant solutions, recommendations or groups from the prioritized list of client-relevant solutions, recommendations or groups. The consulting service is preferably subscription based where the delivery of the recommendations are parsed out to the client over the course of months or years so that the client can easily adopt the recommendations one at a time.

17 Claims, 3 Drawing Sheets

From: Consultant
To: Client Mercy Hospital

Solution/Recommendation #108: *Eliminate antibiotics when culture is negative for the relevant AB(s).*

Rationale/Explanation

- When ABs are used for specific bacteria which is/are now culture-negative, ABs should be immediately stopped (unless clear indications of infection are present, relevant to the proposed ABs).
- Use an "automatic stop order".
- Must have public, active approval/support from chief physician, chief nurse and chief pharmacist, all for infection control, as well as Chiefs of Medicine, Surgery, and Case Management, Chief Nurses for Medicine and Surgery, the CMO/VPMA, CNO, the MEC and the P&T Comm.
- One of the above must be a CEO/COO-designated implementation "champion".
- Policies/procedures/protocols/pathways must be written/disseminated/managed.
- Budget for pharmacy acute ABs should be lowered (adjusted for inflation), creating a cost-reduction goal for the chief pharmacist.

*FIG. 3*

SYSTEMS AND METHODS FOR FACILITATING DELIVERY OF CONSULTING SERVICES

BACKGROUND

1. Field of the Invention

The present invention relates to systems and methods for collecting and disseminating information to facilitate the delivery of consulting services. More particularly, the present invention relates to systems and methods for facilitating the delivery of consulting services to the medical and hospital industry.

2. Background

Consulting is the art of providing expert advice in a particular domain or area of expertise. The traditional consulting model of delivering consulting services is well-established. One or more consultants visit a place of business and/or meet personnel to identify issues or problems that may be detrimentally affecting the business or other undertaking, and then propose solutions to address those issues or problems based on the consultant's experience in the relevant field. Frequently, the consultant will also assist in the implementation of the proposed solutions to better ensure that the solutions are effective.

As those skilled in the art appreciate, consulting services can be expensive. In large part this expense is attributable to the established delivery model. Despite the cost, consultants are able to command relatively high rates of remuneration precisely because they are people who tend to have highly-specialized knowledge in a particular field, and further tend to have the unique ability to apply that knowledge to newly-presented problems and situations. Unfortunately, for many individuals, small businesses and other relatively small, or even medium-sized, enterprises, the price of consulting services is often beyond what is considered affordable, and consequently, such entities tend to not be able to take advantage of the value that consulting services and consultants can provide.

SUMMARY OF THE INVENTION

The present invention provides an improved system and method for the delivery of consulting services. Through experience, the present inventor recognized that in certain industries there are a set of common problems to which standard solutions can be applied. Nonetheless, one size does not necessarily fit all and consultants must tailor "standard" solutions to fit particular client needs. As such, the present inventor has devised a computer-implemented methodology by which a set of predetermined standard solutions can be effectively disseminated to clients, and implemented in appropriate ways.

The present inventor has found that the medical field, in particular, can benefit significantly from the consulting delivery service methodology described herein. Specifically, the present inventor has found that it is possible to easily and efficiently eliminate medically unnecessary supplies and resources in in-patient care.

Embodiments of the present invention comprise identifying, cataloguing and indexing, a relatively large number of solutions or recommendations each of which is preferably immediately implementable. In one possible implementation, the solutions/recommendations are stored in a database that is accessible as described in more detail below. The database preferably remains substantially stable, but may be updated and refined on an on-going basis to ensure that the plurality of solutions/recommendations stored therein remain current and relevant to the industry to which they are directed. In one implementation, each solution/recommendation is uniquely identified by a reference numeral (or any other useful or desirable indexing methodology). The individual solutions/recommendations may also be grouped together in categories.

Once the solutions/recommendations database is available for use, clients are presented with a self-administered assessment, may be conducted online via, e.g., the Internet. The assessment may be in the form of a multiple choice questionnaire that, through appropriate design, is able to quickly and exactingly identify specific categories of issues or problems that are likely being experienced by that client.

With the responses to the assessment in hand, a predetermined process, preferably performed on a computer, then selects and sequences specific recommended solutions/recommendations. That is, in accordance with the principles of the present invention, a predetermined process prioritizes for each client the predetermined solutions that will result in highest potential cost savings value to that client in view of the responses to the assessment.

Once the solutions/recommendations have been selected, sequenced and prioritized, each is preferably then sent electronically (e.g., by email) directly to the client, and preferably to specific persons who have the appropriate level of decision-making power to cause the solutions/recommendations to actually be implemented. Each solution/recommendation or series of solutions/recommendations preferably comes with a described rationale/explanation along with, e.g., 6-8 specific "next steps" to implement the solutions/recommendations. These "next steps" may be presented in bullet form, and all on one screen for quick and simple understanding by the client.

In a preferred subscription-based implementation of the present invention, a single solution/recommendation is provided in this manner every other week for a period of two years, thereby supplying 50 separate and independently implementable solutions/recommendations. Of course, other distribution schedules are also possible and considered to be within the scope of the invention.

In addition, an overall consulting services program may include not only the electronically-provided solutions/recommendations, but may also include follow-up/feedback via, e.g., on-site consulting visits every other month for the same two-year period. Such on-site visits further help to implement the several solutions/recommendations and provide the ability for clients to troubleshoot particularly difficult issues.

The instant consulting services delivery paradigm is particularly useful in the medical field, especially for small to medium-size hospitals. Consulting in the medical and hospital administration field can be particularly expensive. Yet, with the use of the systems and consulting methodologies described herein, these hospitals can still derive considerable value by implementing, in a controlled and methodical manner, a series of solutions/recommendations that quickly and effectively control the hospital's direct and indirect expenses.

The foregoing and other features of the present invention and their attendant advantages will be more fully appreciated upon reading the following detailed description in conjunction with the several associated drawings.

BRIEF DESCRIPTION OF THE DRAWINGS

FIG. 3 illustrates an exemplary email that includes an exemplary cost saving recommendation in accordance with an embodiment of the present invention.

DETAILED DESCRIPTION

Figure 1:
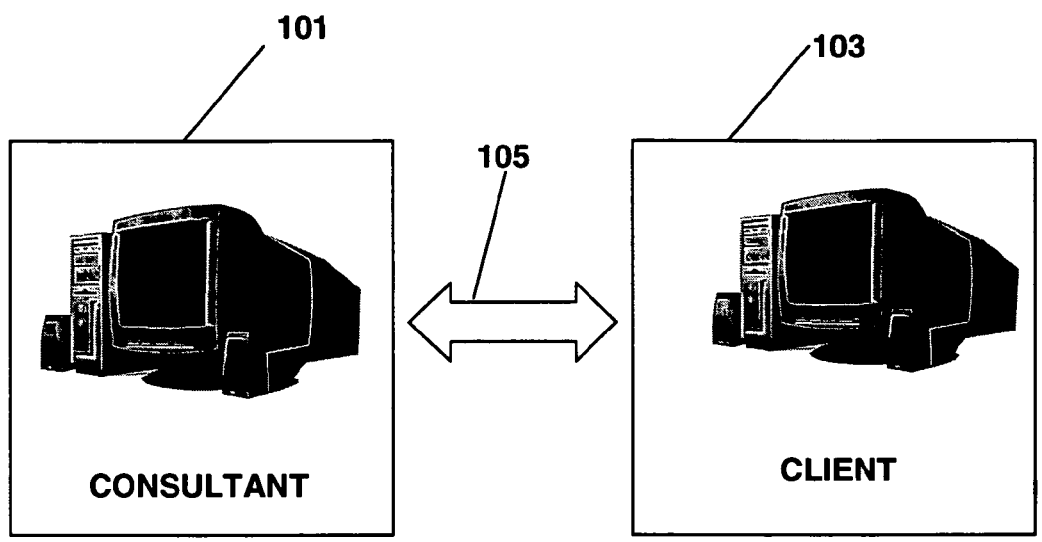
FIG. 1 illustrates the relationship between a consultant and a client in accordance with an embodiment of the present invention.

FIG. 1 illustrates the relationship between a consultant 101 and a client 103 in accordance with an embodiment of the present invention. In a preferred embodiment of the present invention, consultant 101 and client 103 (such as a hospital), are in communication both electronically (e.g., via the internet) and in person, as schematically shown by reference numeral 105. As noted above, traditional consulting often involves, preliminarily, visiting a place of business and/or meeting with personnel to identify issues or problems that may be detrimentally affecting the business or other undertaking, and only then proposing solutions to address those issues or problems, all based on the consultant's experience in the relevant field. Frequently, the consultant will also assist with the implementation of the proposed solutions to better ensure that the solutions will result in the intended effects.

Embodiments of the present invention eliminate substantially, or perhaps entirely, the need for a consultant to conduct that preliminary on-site visit, and thereby, an immediate, and substantial, cost savings is realized by the client. Instead of spending a significant amount of time analyzing what problems or issues a particular client might have, embodiments of the present invention allow clients to reap results from consulting services almost immediately.

Figure 2:
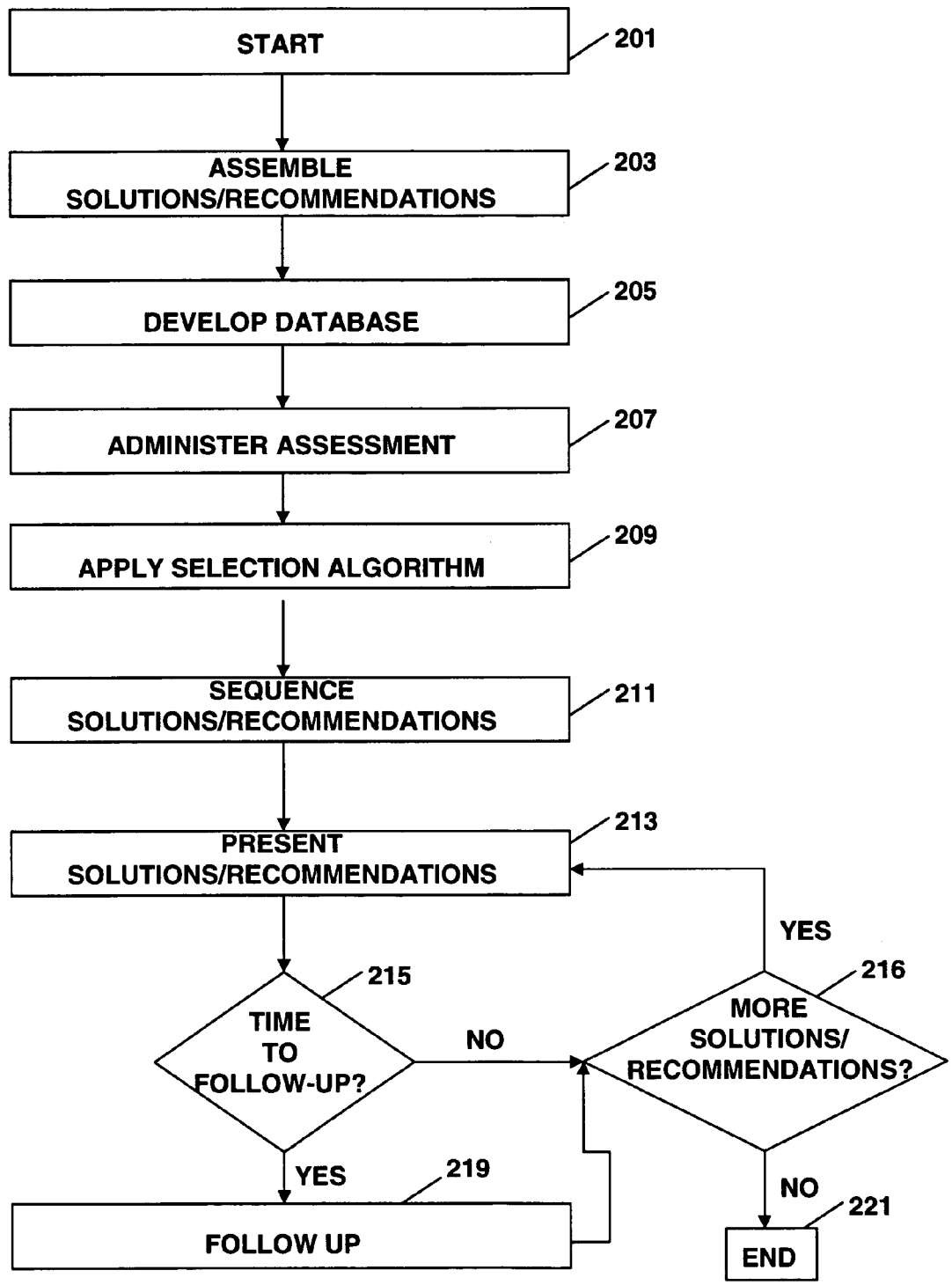
FIG. 2 is an exemplary flow chart illustrating a method of providing consulting services in accordance with an embodiment of the present invention.

Reference is now made to FIG. 2, which depicts an exemplary methodology or process that begins at step 201, and then immediately flows to step 203 where a plurality of solutions/recommendations are assembled. Each solution/recommendation is uniquely identified, catalogued, and indexed. This process may also include grouping selected solutions/recommendations together that tend to work well together and maximize cost savings when used in connection with one another. A primary, though not critical, attribute of each solution/recommendation is that it is preferably immediately implementable. That is, each solution/recommendation is preferably relatively simple to implement by, e.g., slightly modifying standard operating procedures to optimize the use of equipment, avoid wasteful use of equipment, or avoid unnecessary procedures altogether. A list of several solutions/recommendations that may be used in conjunction with the present invention, in the context of hospital administration, appears near the end of this description.

Once the solutions/recommendations are assembled, they are stored in a database, as shown at step 205. This database may be part of a computer system belonging to consultant 101. The database may be any type of database known to those skilled in the art. The solutions/recommendations could be stored, for example, in a relational database to facilitate the establishment of relationships among the different entries. However, the type of database used is not critical.

The database preferably remains substantially stable, but may be updated and refined on an on-going basis to ensure that the plurality of solutions/recommendations stored therein remain current and relevant to the industry to which they are directed.

Once the solutions/recommendations database is available for use, clients are presented with a self-administered assessment (step 207) that may be conducted online via, e.g., the Internet. The assessment may be in the form of a multiple choice questionnaire that, through careful design, is able to quickly and exactingly identify specific categories of issues or problems that are likely being experienced by the client. An exemplary assessment follows immediately below:

Pre-Implementation Mini-Assessment (Example)

Please select the best answer by clicking on the line of your choice. "Guesstimates" are very acceptable. (This should not take more than 20 minutes.)
1. Do you have a cardiac cath lab?
   A____ Yes
   B____ No
2. Do you use femoral closure devices in your cath lab?
   A____ We don't have a cath lab.
   B____ Yes
   C____ No
   D____ Haven't a clue.
3. How many femoral closure devices do you use per year?
   A____ We have no cath lab
   B____ Less than 100
   C____ Between 100 and 500
   D____ Between 500 and 1500
   E____ Greater than 1500
   F____ Have no idea.
4. How many hours post-closure are prophylactic antibiotics given?
   A____ Less than 24 hours.
   B____ Between 24 and 36 hours.
   C____ Between 36 and 48 hours
   D____ Greater than 48 hours.
   E____ Have no idea.
5. Do you do in-patient dialysis?
   A____ Yes
   B____ No
   C____ Don't know
6. If yes, roughly how many dialyses per year occur on day of discharge?
   A____ We don't have in-patient dialysis.
   B____ I don't have a clue.
   C____ Less than 25.
   D____ Between 25 and 100.

| Pre-Implementation Mini-Assessment (Example) |
|---|
|     E___ Between 100 and 200.<br>    F___ Greater than 200.<br>7. Do you offer in-patient sleep studies?<br>    A___ Yes<br>    B___ No<br>    C___ Don't know<br>8. If yes, how many in-patient sleep studies do you do per year?<br>    A___ We don't do in-patient sleep studies.<br>    B___ Less than 50.<br>    C___ Between 50 and 150.<br>    D___ Greater than 150.<br>    E___ Have no idea.<br>9. Do you outsource any major, non-clinical areas, eg, food, laundry?<br>    A___ Yes<br>    B___ No<br>    C___ Don't know<br>10. Are the employees who do the work, your employees on your direct payroll, or are they employees of the outsource vender?<br>    A___ We do no major service outsourcing.<br>    B___ Yes, we directly employ these staff, but they are managed by the vender.<br>    C___ No, the vender directly employs all these staff,eg, food staff.<br>    D___ Have no idea.<br>11. How many in-patient lipid studies do you do per year?<br>    A___ Have no idea.<br>    B___ Less than 50<br>    C___ Between 50 and 100.<br>    D___ Between 100 and 300.<br>    E___ Greater than 300.<br>12. Do you have a dedicated billing analyst just for the ED?<br>    A___ Yes<br>    B___ No<br>    C___ Have no idea.<br>13. What % of your re-processable devices are re-processed?<br>    A___ Don't have a clue.<br>    B___ Between 5 and 10%<br>    C___ Between 10 and 20%<br>    D___ Between 20 and 40%<br>    E___ Between 40 and 70%<br>    F___ Greater than 70%<br>14. Do you a wound care program?<br>    A___ Yes<br>    B___ No<br>    C___ Don't know<br>15. If yes, do you outsource it?<br>    A___ We don't have a wound care program.<br>    B___ Yes, we outsource it.<br>    C___ No, we don't outsource it.<br>    D___ Have no idea.<br>16. Do you buy used/certified medical equipment?<br>    A___ Yes, often<br>    B___ Yes, but rarely<br>    C___ No<br>    D___ Have no idea.<br>17. How often, on average, does your staff change unsoiled bed linen for the same pt.?<br>    A___ More than once a day.<br>    B___ Once a day.<br>    D___ Once every other day.<br>    E___ Once every ri day<br>    F___ Have no idea.<br>18. Do you own your own food/snack vending machines?<br>    A___ Yes<br>    B___ No<br>    C___ Have no idea.<br>19. Do you use an automated time and attendance system (ATTS) for all your hourly employees?<br>    A___ Yes<br>    B___ No<br>    C___ Have no idea.<br>20. Do your IT contracts have opt-out clauses for unused and/or unwanted and/or uneeded apps.?<br>    A___ Yes<br>    B___ No<br>    C___ Have no idea.<br>21. Do you take advantage of and/or utilize IT opt-out clauses?<br>    A.___ Yes, but rarely<br>    B.___ Yes, sometimes to often<br>    C.___ No<br>    D.___ Don't know. |

| Pre-Implementation Mini-Assessment (Example) |
|---|

22. Do you ever directly use para-legals for legal work?
    A.____ Yes, often
    B.____ Yes, but rarely
    C.____ No
    D.____ Don't know
23. Do you use disposable linens, textiles, and/or washcloths, etc. for pts. with no infection precaution designation?
    A.____ Yes, very frequently
    B.____ Yes, often
    C.____ Yes, but not much
    D.____ Have no idea
24. Do you have acute rehab and/or mental health beds?
    A.____ Yes
    B.____ No
    C.____ Don't know
25. If you have acute rehab and/or mental health beds, is either service losing money.
    A.____ Yes
    B.____ No
    C.____ Have no idea
    D.____ We have no rehab or mental health beds
26. Do you have automated DRG coding?
    A.____ Yes
    B.____ No
    C.____ Don't know
27. If you do have automated DRG coding, is it integrated with your billing IT?
    A.____ Yes
    B.____ No
    C.____ Don't know
    D.____ We don't have automated DRG coding.
28. Do you use, audit and routinely enforce in your supplier/vendor contracts "failure to supply" clauses?
    A.____ Yes, routinely.
    B.____ Yes, sometimes.
    C.____ Yes, but rarely.
    D.____ No
    E.____ Have no idea.
29. How many over-night/next day express envelopes/packages do you send in an average week?
    A.____ 0-10
    B.____ 10-30
    C.____ 30-60
    D.____ more than 60
30. Do you use agency nurses?
    A.____ Yes
    B.____ No
    C.____ Don't know
31. If you do use agency nurses, how many agencies do you use?
    A.____ We don't use agency nurses.
    B.____ 1
    C.____ 2
    D.____ 3 or more
    E.____ Don't know
32. Approximately how many acute in-pt. MRIs and/or PETs do you do per month?
    A.____ None
    B.____ 5-25
    C.____ 25-100
    D.____ More than 100
    E.____ Have no idea.
33. For out-pts. seen on an elective basis, what % are asked for payment, whole or partial, prior to treatment?
    A.____ 0%
    B.____ 1-10%
    C.____ 10-30%
    D.____ 30-70%
    E.____ more than 70%
    F.____ Have no idea
34. For in-pts. seen on an elective basis, what % are asked for payment, whole or partial, prior to treatment?
    A.____ 0%
    B.____ 1-10%
    C.____ 10-30%
    D.____ 30-70%
    E.____ More than 70%
    F.____ Don't know.
35. What % of your pregnancy admissions receive a C-section after an initial, prior-admit, C-section?
    A.____ 0-5%
    B.____ 5-15%
    C.____ 15-25%

| Pre-Implementation Mini-Assessment (Example) |
| --- |

D.\_\_\_ 25-40%
    E.\_\_\_ 40-70%
    F.\_\_\_ More than 70%
    G.\_\_\_ Don't know.
36. Does your hospital have a Web site?
    A.\_\_\_ Yes
    B.\_\_\_ No
    C.\_\_\_ Don't know.
37. Does your hospital do any fund-raising from any of its Web sites?
    A.\_\_\_ We don't have a hospital web site.
    B.\_\_\_ Yes
    C.\_\_\_ No
    D.\_\_\_ Don't know.
38. Does your hospital use internet-based "skip-tracing"?
    A.\_\_\_ No or rarely
    B.\_\_\_ Sometimes
    C.\_\_\_ Often
    D.\_\_\_ Frequently
    E.\_\_\_ Have no idea
39. Does your hospital use generic exam gloves and generic electrodes?
    A.\_\_\_ No or rarely
    B.\_\_\_ Sometimes
    C.\_\_\_ Often
    D.\_\_\_ Frequently
    E.\_\_\_ Always
    F.\_\_\_ Have no idea.

With the responses to the assessment in hand, a predetermined process or selection algorithm is then applied at step 209. This step may be performed on a computer and, based on the responses to the assessment, selects and sequences specific recommended solutions/recommendations from the database. In other words, the selection algorithm prioritizes for each client solutions that will result in highest potential savings value to that client at the earliest possible date in view of the responses to the assessment. For example, if, in the context of hospital administration, a given solution/recommendation is to modify certain procedures for dialysis, but from the assessment it is determined that the client hospital does not perform in-patient dialysis, that particular solution/recommendation would be eliminated from being suggested to the client in the first place. A portion of a relatively simple selection algorithm is outlined below (Catalog #'s 101-105 are provided near the end of this description):

| Order | Catal.# | Sol. Desc | Exception/Eliminate |
| --- | --- | --- | --- |
| 1 | #101 | Post-Clos. ABs | If Q4 = A or B |
| 2 | #102 | Fem. Clos. Dev | If Q1 = B; Q2 = A, C; Q3 = A, B |
| 3 | #103 | Dialysis Day/Dis | If Q5 = B; Q6 = A, B |
| 4 | #104 | DNR | 0 |
| 5 | #105 | In-Pt. Sleep | If Q7 = B; Q8 = A, B |
| 6 | #106 | Low-waged EEs | If Q9 = B; Q10 = A, C |
| 7 | #107 | In-Pt. Endos | 0 |

The selection algorithm or process of step 209 customizes sequence and selection of the solutions/recommendations for each client based on each client's completed assessment/questionnaire. The process prioritizes for each client solutions which constitute the "lowest hanging fruit", i.e., those solutions that have the highest potential value (e.g., biggest savings potential and as soon as possible for each client).

Referring to the tabular selection algorithm above, the sequence/order of solutions/recommendations sent to clients follows a predetermined order, except as noted in the "exception/eliminate" column on the right.

The "exception/eliminate" column refers to the Question # on the assessment/questionnaire. "Q #"=the Question #'s response. The response in turn represents the Solution to be eliminated from that client's Solution "menu."

For example, Order 1, indicates that Catalogue Solution #101 is sent to the client first, unless Question 4 on the assessment/questionnaire is checked off as an A or B.

Once the solutions/recommendations have been selected, sequenced and prioritized, each is preferably then presented to the client successively, as indicated by step 211 (and other steps described below). In a preferred embodiment, each solution/recommendation is sent electronically (e.g., by email) directly to the client, and preferably to specific persons having the appropriate level of decision-making power to act on and implement the solutions/recommendations (such as a hospital administrator). Each solution/recommendation or series of solutions/recommendations preferably also comes with a described rationale/explanation along with, e.g., 6-9 specific "next steps" to implement the solutions/recommendations. These "next steps" may be presented in bullet form, and all on one screen for quick and simple understanding by the client. FIG. 3 shows an exemplary bulletized solution/recommendation email that includes a rationale/explanation portion.

In an embodiment, a method for delivering consulting services includes: assembling a plurality of solutions or recommendations designed to promote cost savings and improved operational efficiency; categorizing at least a subset of the plurality of solutions or recommendations into groups; selecting and sequencing client-relevant solutions, recommendations or groups from the plurality of solutions, recommendations or groups based on information received from a client; prioritizing the client-relevant solutions, recommendations or groups into a prioritized list of client-relevant solutions, recommendations or groups; and successively presenting to the client, over a predetermined amount of time, each of the client-relevant solutions, recommendations or groups from the prioritized list of client-relevant solutions, recommendations or groups.

An overall consulting services delivery program in accordance with the principles of the present invention not only includes the electronically-provided solutions/recommendations, but may also include follow-up opportunities for feedback via, e.g., on-site consulting visits. As shown in FIG. 2 at step 215, it is determined whether it is time for the consultant to follow-up with the client. This follow-up step (step 219) could follow a predetermined schedule, e.g., every other month for a predetermined number of years, or follow-up could be provided on an as-needed basis, depending on the client's need. Different pricing models may be associated with each of these options as well.

On-site follow-up visits may help to implement the several solutions/recommendations that have been presented and provide the ability for clients to trouble shoot particularly difficult issues.

After the opportunity for follow-up, or if no follow-up was conducted, it is then determined at step 216, whether the client is entitled to still more solutions/recommendations. If not, the process ends at step 221. If more solutions/recommendations are to be presented to the client, then the process loops back to step 213. In a "subscription" implementation, one solution/recommendation is provided via at least steps 213 and 216 every other week for a period of two years, thereby supplying to the client 50 separate and independently implementable solutions/recommendations. Of course, other distribution schedules may be implemented.

The instant consulting methodology has found particular utility in the medical field, especially for small to medium-size hospitals that can realize considerable cost savings by implementing, in controlled and methodical manner, a series of solutions/recommendations that quickly and effectively control direct and indirect expenses.

As mentioned herein, client 103 and consultant 101 are preferably in communication with each other, at least electronically, via email or the world wide web. The world wide web may be used, for example, to administer the assessment to gather the initial information necessary for the consultant to prioritize the relevant solutions/recommendations for the client. Technology to enable email and the world wide web is well-known to those skilled in the art and is therefore not described herein in detail.

The assessment itself, as mentioned, is preferably a multiple choice questionnaire that can be easily completed by someone having the appropriate knowledge. Then, using the selection algorithm (which may be thought of as a decision tree for example), appropriate solutions/recommendations can be selected from the database of solutions/recommendations and successively presented to the client.

Pricing models can vary for the consulting services described herein in accordance with the present invention. In one possible model, a client may pay for a single most relevant solution/recommendation, without being entitled to further service. Alternatively, a client may elect to pay for each solution/recommendation individually under a program whereby if payment is received by a certain date, the next appropriately selected solution/recommendation is delivered to the client. In perhaps the most preferably and economical model, a client may subscribe to the consulting services in accordance with the present invention whereby for a set fee for a predetermined period (e.g., one or two years), the client will receive successive solutions/recommendations targeted for their particular situation, and further be entitled to follow-up consulting services including on-site visits. This latter model aligns most clearly with the exemplary consulting methodology depicted by the flow chart in FIG. 2.

Embodiments of the present invention may also be used to conduct audits of businesses or other enterprises. Stated otherwise, rather than having the client receive multiple solutions/recommendations for the client to implement, the plurality of solutions/recommendations may be used directly by consultants to conduct audits of businesses or enterprises. Consultants can use the plurality of solutions/recommendations as a guide to assess the operations and efficiency of a given enterprise.

The greatest opportunity for achieving maximal dollar savings in supply chain/resource management is in the area of supply UTILIZATION (vs. contract maximization, tiered pricing, price per widget, etc.). The present invention focuses, in many respects on supply utilization reduction. (Standardization is viewed as a sub-set of utilization and is not a key part of the instant invention.)

The present invention may also be viewed and used as a revenue cycle management enhancer, by, e.g., increasing ICU through-put, by ensuring that patients are handled in the most efficient manner while in the ICU. Many solutions/recommendations both decrease supply costs and increase revenue.

The present invention may work best in a multi-hospital system composed of large, medium and small hospitals, as the methodology can produce both "quick hit" successes and decreased system variability (i.e., improved "system-ness") in both supply chain management and revenue cycle management, as well as in medical management, thereby creating opportunities for other, integrated, service up-sells.

As noted, the solutions/recommendations are preferably highly and immediately implementable, i.e., there is a very rapid speed to solution. In fact, it is believed that the instant methodology has the fastest and most transparent approach in the supply cost management business. In effect, the instant methodology starts with the solution. As a result, the present invention is believed to be faster, cheaper, better, and simpler to implement than more conventional approaches.

Moreover, the present invention produces relatively easy-to-measure, valuable outcomes. Once a given solution/recommendation is actually put in place, savings can be easily quantified.

In addition to the features described already, the present invention may also include an integrated Help Desk for phone, voice mail and e-mail contact, with all implementation questions responded to on a timely basis, e.g., within one business day.

Also, various user-group configurations and formats can be implemented, so users can share their discoveries and practical insights, and even engage in selected, collaborative supply/resource savings activities. Indeed, the instant methodology is highly complementary, and very synergistic, with Lean 6 Sigma and similar implementation-oriented approaches.

Exemplary Solutions/Recommendations for Eliminating Medically Unnecessary Supplies/Resources in In-Patient Care:

101. Eliminate Antibiotics (Abs) after 24-Hours Post-Closure

Prophylactic ABs after 24 hours post-closure are medically unnecessary, (unless clear indications of infection are present), costly and lead to dangerous AB-resistant "super" infections.

Unless there is evidence of post-op infection, stop ABs within 24 hours or less of closure, for non-CV cases (some CV cases may go to 48 hours post-closure).

Must initially gain public, active approval/support from chief physician, chief nurse and chief pharmacist, all for infection control, as well as from physician chief of the surgical unit, chief surgical nurse, CMO/VPMA, CNO, Director of the surgical unit/division, chief surgical case manager, the MEC and P&T Comm.

One of the above must be a CEO/COO-designated implementation "champion".

Policies/procedures/protocols/paths need to be developed/disseminated/managed, eg, "automatic stop orders" at 24 hours.

Budget for pharmacy post-op ABs should be lowered, adjusted for inflation, creating a cost-reduction goal for the chief pharmacist.

CMS's Hospital Compare site now publicly rates hospitals on their achieving this 24 hour-stop goal.

102. Eliminate Femoral Closure Devices.

95-98% of femoral closure devices are not medically necessary, can be safely replaced by thumb pressure, or more expensively, by a $50 patch.

If use a patch in place of closure device, do not use stitch technology.

Savings are around $205 per device not used.

Dozens of hospitals have safely/successfully eliminated 95%-plus of these medically unnecessary devices.

Requires public, active approval/support from Cath Lab Chief Cardiologist, the Director of the Cath Lab, senior Cath Lab RNs, the CMO/VPMA, the CNO and the MEC.

One of the above must be a CEO/COO-designated implementation "champion".

Thumb pressure requires more time from Cath Lab techs (non-RNs/non-LPNs), eg, 30 minutes per patient.

Policies/procedures/protocols/paths need to be written/disseminated/managed.

Budget for cath lab closure devices should be drastically lowered, creating a cost-reduction goal for Cath Lab managers.

103. Eliminate 80-95% of Acute Day-of-Discharge Dialysis.

Most day-of-discharge dialysis can be done as an out-pt. procedure. Can discharge pt. by 11 AM to send pt. to out-pt. setting, even if on hospital campus.

May need to pay for transportation, which can be very cost effective.

Most dialysis pts. are on Medicare. Therefore, if hospital owns an out-pt. dialysis unit, hospital can save dialysis costs from acute DRG and gain a revenue from an out-pt. service.

Must work closely with and obtain public, active approval/support from CNO, Chief of Case Management, CMO/VPMA, Chief of Medicine, Chief Nephrologist, Director of Dialysis services and the MEC.

One of the above must be a CEO/COO-designated implementation "champion".

Policies/procedures/protocols must be written/disseminated/managed.

Budget for in-pt. last day dialysis should be lowered, creating a cost-reduction goal for this service and its relevant managers.

104. Avoid Resuscitation of all DNR-Designated pts.

5-15% of all DNR-labeled pts. are inappropriately, expensively and illegally resuscitated.

Each inappropriately resuscitated DNR pt. costs hospital $10 K-$40 K in add-on costs, not counting potential litigation costs.

Most incorrect resuscitations/"blue codes" can be avoided with better, bigger and more pt. labeling on chart, wrist band (coded), crash cart, and in-house training.

Make sure all pts. & their families at admission/pre-admission are explicitly and clearly asked about their DNR preferences. This should be a scripted process.

Less than half of pts./families who want DNR orders actually get them.

Must initially gain public, active approval/support from CMO/VPMA, CNO, Chief of Medicine, Chief Case Manager, the MEC and all Rapid Response Team leaders.

One of the above must be a CEO/COO-designated implementation "champion".

Policies/procedures/protocols must be written/disseminated/implemented.

105. Eliminate in-pt. Sleep Studies.

98-100% of all in-pt. sleep studies, eg, for apnea, should not be done on an in-pt. basis.

May want to simply eliminate all in-pt. sleep studies for: ease of management, increased out-pt. revenues, and decreased costs.

This is particularly true for DRG re-imbursed pt. diagnoses.

Hospital should have/develop its own out-pt. sleep studies center, esp. given how lucrative and crowded most sleep centers are.

Your out-pt. sleep centers should be heavily promoted (or built).

Diversion from in-pt. to out-pt. requires public, active approval/support from Chief of Medicine, CMO/VPMA, CNO, Chief of Case Management, the MEC.

One of the above must be a CEO/COO-designated implementation "champion".

Policies/procedures/protocols must be written/disseminated/managed.

Budget for in-pt. sleep studies should be nearly/totally eliminated, creating a cost-reduction goal for the relevant managers.

The foregoing disclosure of the preferred embodiments of the present invention has been presented for purposes of illustration and description. It is not intended to be exhaustive or to limit the invention to the precise forms disclosed. Many variations and modifications of the embodiments described herein will be apparent to one of ordinary skill in the art in light of the above disclosure. The scope of the invention is to be defined only by the claims appended hereto, and by their equivalents.

Further, in describing representative embodiments of the present invention, the specification may have presented the method and/or process of the present invention as a particular sequence of steps. However, to the extent that the method or process does not rely on the particular order of steps set forth herein, the method or process should not be limited to the particular sequence of steps described. As one of ordinary skill in the art would appreciate, other sequences of steps may be possible. Therefore, the particular order of the steps set forth in the specification should not be construed as limitations on the claims. In addition, the claims directed to the method and/or process of the present invention should not be limited to the performance of their steps in the order written, and one skilled in the art can readily appreciate that the sequences may be varied and still remain within the spirit and scope of the present invention.

What is claimed is:

1. A computer implemented method for facilitating delivery of hospital consulting services to an administration entity of a hospital, comprising:

providing a computer readable database having stored therein a plurality of hospital and patient care cost saving recommendations;

offering a self-assessment questionnaire to an administration entity of a hospital;

collecting responses from the administration entity responsive to the self-assessment questionnaire;

categorizing at least a subset of the plurality of recommendations into groups;

selecting, by a computer, a plurality of applicable recommendations or groups from the plurality of recommendations, the selection being based on the responses to the self-assessment questionnaire;

establishing, by the computer, a sequence and priority to the plurality of applicable recommendations or groups by prioritizing the plurality of applicable recommendations or groups by a highest potential savings value to the administration entity at an earliest possible date in view of the responses provided in the self-assessment questionnaire;

creating a distribution schedule based on the established sequence and priority and based on a scheduling preference of the administrative entity; and implementing the distribution schedule for the plurality of applicable recommendations or groups, including successively and separately presenting each one of the plurality of applicable recommendations or groups to the administrative entity in accordance with the distribution schedule.

2. The method of claim 1, wherein the self-assessment questionnaire is offered over the Internet.

3. The method of claim 1, wherein successively and separately presenting each one of the plurality of applicable recommendations or groups comprises sending an email that includes one of the plurality of applicable recommendations or groups.

4. The method of claim 3, wherein the one of the plurality of applicable recommendations or groups is immediately implementable.

5. The method of claim 1, further comprising providing on-site consulting visits to the hospital.

6. The method of claim 1, wherein the hospital consulting services are provided on a subscription basis.

7. The method of claim 1, wherein recommendations that are not implementable by the administration entity are eliminated from being suggested to the administration entity.

8. The method of claim 6, wherein the scheduling preference is based on the subscription basis.

9. The method of claim 1, wherein the administrative entity is billed separately for each of the plurality of applicable recommendations or groups.

10. The method of claim 9, further comprising waiting until payment is received for a previous one of the plurality of applicable recommendations or groups before presenting a next one of the plurality of applicable recommendations or groups in accordance with the distribution schedule.

11. The method of claim 1, further comprising providing a help desk to respond to implementation questions.

12. The method of claim 11, wherein the help desk may be contacted via phone, voice mail, or e-mail.

13. The method of claim 1, further comprising providing a rationale or explanation with each one of the plurality of applicable recommendations or group.

14. The method of claim 1, further comprising providing a plurality of identifiable steps with each one of the plurality of applicable recommendations or groups that provide guidance on implementing the one of the plurality of applicable recommendations or groups.

15. The method of claim 14, wherein the identifiable steps are provided in bullet form.

16. The method of claim 1, wherein the computer readable database is periodically updated or refined to ensure that the recommendations stored therein are relevant to the medical and hospital industry.

17. The method of claim 1, wherein the distribution schedule provides for presenting one of the plurality of applicable recommendations or groups every other week for a period of two years.

* * * * *